United States Patent
Balcke et al.

(10) Patent No.: US 9,610,231 B2
(45) Date of Patent: Apr. 4, 2017

(54) COSMETIC OR DERMATOLOGICAL PREPARATION FOR APPLICATION ON WET SKIN

(75) Inventors: Isabel Balcke, Hamburg (DE); Rainer Kroepke, Schenefeld (DE); Sabine Schulz, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 581 days.

(21) Appl. No.: 13/606,536

(22) Filed: Sep. 7, 2012

(65) Prior Publication Data

US 2013/0108572 A1    May 2, 2013

(30) Foreign Application Priority Data

Oct. 31, 2011 (DE) .................. 10 2011 085 500
Jan. 10, 2012 (DE) ................... 20 2012 000 164 U

(51) Int. Cl.
| A61K 8/92 | (2006.01) |
| A61Q 9/02 | (2006.01) |
| A61Q 19/00 | (2006.01) |
| A61K 8/34 | (2006.01) |
| A61K 8/81 | (2006.01) |
| A61K 8/31 | (2006.01) |

(52) U.S. Cl.
CPC ............... *A61K 8/342* (2013.01); *A61K 8/31* (2013.01); *A61K 8/8147* (2013.01); *A61K 8/8152* (2013.01); *A61Q 9/02* (2013.01); *A61Q 19/00* (2013.01); *A61K 2800/33* (2013.01); *A61K 2800/594* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| 5,723,420 | A | 3/1998 | Wei et al. |
| 5,928,632 | A | 7/1999 | Reusch |
| 7,005,557 | B2 | 2/2006 | Klofta et al. |
| 7,338,928 | B2 | 3/2008 | Lau et al. |
| 7,368,122 | B1 | 5/2008 | Dow et al. |
| 7,449,613 | B2 | 11/2008 | Klofta et al. |
| 7,776,347 | B2 | 8/2010 | Kerschner et al. |
| 8,394,500 | B2 | 3/2013 | Beumer et al. |
| 9,237,995 | B2 | 1/2016 | Coffindaffer et al. |
| 2002/0007055 | A1 | 1/2002 | Uchiyama et al. |
| 2003/0077307 | A1 | 4/2003 | Klofta et al. |
| 2005/0124530 | A1 | 6/2005 | Creutz et al. |
| 2005/0143282 | A1 | 6/2005 | Creutz et al. |
| 2005/0148544 | A1 | 7/2005 | Uchiyama et al. |
| 2006/0064068 | A1 | 3/2006 | Klofta et al. |
| 2006/0239953 | A1* | 10/2006 | Clapp et al. ............... 424/70.22 |
| 2006/0251606 | A1 | 11/2006 | Coffindaffer et al. |
| 2008/0220031 | A1* | 9/2008 | Wunsch et al. ............... 424/401 |
| 2009/0041697 | A1 | 2/2009 | Klofta et al. |
| 2009/0281013 | A1* | 11/2009 | Patel et al. .................... 510/158 |
| 2010/0069601 | A1 | 3/2010 | Baumer |
| 2011/0071223 | A1 | 3/2011 | Ishii et al. |
| 2011/0243863 | A1 | 10/2011 | Kawa et al. |
| 2014/0018276 | A1 | 1/2014 | Coffindaffer et al. |
| 2014/0044666 | A1 | 2/2014 | Uchiyama et al. |

FOREIGN PATENT DOCUMENTS

| DE | 102006034320 A1 | 1/2008 |
| DE | 102007024377 A1 | 11/2008 |
| DE | 102008052520 A1 | 4/2010 |
| EP | 1479378 A1 | 11/2004 |
| EP | 1541121 A1 | 6/2005 |
| EP | 2174639 A1 | 4/2010 |
| JP | 2010209293 A | 9/2010 |
| WO | 9732569 | 9/1997 |
| WO | 0027271 A2 | 5/2000 |
| WO | 02092043 A2 | 11/2002 |
| WO | 03004070 A1 | 1/2003 |
| WO | 03083031 A1 | 10/2003 |
| WO | 2006094309 A2 | 9/2006 |
| WO | 2007144189 A2 | 12/2007 |

OTHER PUBLICATIONS

U.S. Appl. No. 13/606,570, filed Sep. 7, 2012; Inventors: Isabel Balcke et al.

* cited by examiner

*Primary Examiner* — Robert A Wax
*Assistant Examiner* — Randeep Singh
(74) *Attorney, Agent, or Firm* — Abel Law Group, LLP

(57) ABSTRACT

An aqueous cosmetic or dermatological preparation for application on wet or moist skin which is substantially emulsifier-free and comprises at least two different polyacrylic acid polymers, at least two different $C_{14-22}$ fatty alcohols, and at least about 13% by weight of microcrystalline wax, preferably in combination with one or more hydrocarbon oils.

32 Claims, No Drawings

COSMETIC OR DERMATOLOGICAL PREPARATION FOR APPLICATION ON WET SKIN

CROSS-REFERENCE TO RELATED APPLICATIONS

The present application claims priority under 35 U.S.C. §119 of German Patent Application No. 10 2011 085 500.9, filed Oct. 31, 2011, and German Utility Model Application No. 20 2012 000 164.7, filed Jan. 10, 2012. The entire disclosures of these documents are expressly incorporated by reference herein.

BACKGROUND OF THE INVENTION

1. Field of the Invention

The present invention relates to a substantially emulsifier-free cosmetic or dermatological preparation comprising polyacrylic acid polymers, fatty alcohols and microcrystalline wax. The preparation is suitable for application to skin (in particular, wet or moist skin) and thus permits rubbing cream in while showering.

2. Discussion of Background Information

Cosmetic or dermatological preparations can be divided on the basis of their application time and their application purpose. Some products are immediately washed off after application ("rinse-off"), others are intended to remain on the skin for longer periods of time and are effective there ("leave-on").

Cosmetic preparations for skin care are primarily developed for application to dry skin. This form of preparations are known as leave-on preparations, such as creams, lotions or body milk. Often, these are formulated as emulsions, in particular W/O, O/W, O/W/O or W/O/W emulsions.

Emulsions are generally understood as meaning heterogeneous systems which comprise two liquids that are immiscible or only miscible to a limited extent and which are usually referred to as phases. In an emulsion, one of the two liquids (water or oil) is dispersed in the form of very fine droplets in the other liquid. The liquids (pure or in the form of solutions) are present in an emulsion in a more or less fine distribution, which is generally only stable to a limited extent.

If the two liquids are water and oil and oil droplets are present in fine distribution in water, then this is an oil-in-water emulsion (O/W emulsion, e.g. milk). The basic character, for example electrical conductivity, sensory properties, ability of the continuous phase to stain, of an O/W emulsion is defined by the water. In the case of a water-in-oil emulsion (W/O emulsion, e.g. butter), the principle is reversed, the basic character here being determined by the oil.

Leave-on preparations are not suitable for application to wet or moist skin. Due to the emulsifiers present, they are able to emulsify water and, due to the lipids, in some cases leave behind an oily film.

Rinse-off preparations are designed for application under the shower or during bathing. By contrast, rinse-off preparations, however, involve to a lesser extent the care aspect as is obtained upon rubbing cream in.

It is desirable to provide a preparation which exhibits a skin care effect and can also be applied as rinse-off, for example under the shower.

One property of cosmetic products that is very important to the consumer but can only be measured quantitatively with difficulty is their texture and sensory properties. The term "texture" is understood as meaning those properties of a cosmetic which can be attributed to the constitution of the preparation, perceived by sense of feel and touch and in some cases expressed in terms of mechanical or rheological flow properties. The texture can be tested in particular by means of sensorics. The texture of cosmetic products, which can optionally be influenced with the help of additives, is of virtually identical importance to the consumer as their effects which can be ascertained objectively.

The term "sensorics" refers to the scientific discipline which deals with the evaluation of cosmetic preparations on the basis of sensory impressions. The sensory assessment of a cosmetic is made on the basis of the visual, olfactory and haptic impressions.

Visual impressions: all features that can be perceived by eye (color, shape, structure).

Olfactory impressions: all scent impressions that can be perceived upon breathing in air through the nose, which can often be differentiated into initial scent (top note), main scent (medium note, body) and after-scent (base note). The volatile substances only released upon application also contribute to the olfactory impression.

Haptic impressions: all sensations of the sense of touch which concern primarily constitution and consistency of the product.

The sensory analysis makes use of the possibility of ascertaining the overall sensory impression of a product integrally. Disadvantages of sensory analysis are the subjectivity of the impression, the ease with which test subjects can be influenced and the considerable scattering of the results brought about as a consequence. These failings are nowadays countered by using groups of trained test subjects, mutual shielding of the testers, and statistical evaluation of the mostly extensive analytical data.

It was therefore a further object of the present invention to provide preparations which, besides the criteria customary for cosmetics such as compatibility, storage stability and the like, also offer the consumer essential, hitherto unknown cosmetic, in particular sensory, benefits. In particular, the sought preparations should be suitable for use in the body care sector, i.e. for application to the entire body and at the same time be sensorily attractive.

EP 1 390 006 A2, the entire disclosure of which is incorporated by reference herein, discloses oil-in-water emulsions for application to wet skin. The preparations of EP 1 390 006 A2 comprise water, a dispersion stabilizer, a structured oil phase and structurant, which form a stable network of distantly distributed solids in the liquids. Besides preferred inorganic structurants, solid fatty acid esters and vaseline are specified inter alia as organic structurants. Sensory modifiers specified are additionally nonionic polymers such as polyethylene oxide, polyvinyl alcohol, polyvinyl acetate pyrrolidones, anionic polymers such as polyaspartate, polymaleates and sulfonates, cationic polymers and mixtures thereof.

EP 2 174 639 A2, the entire disclosure of which is incorporated by reference herein, discloses oil-in-water emulsions for application to wet skin. The preparations comprise water-soluble polymer, pasty oils and liquid oil in combination with a large amount of glycerol. Examples of water-soluble polymers are inter alia natural polymers such as vegetable polysaccharides, animal proteins, semi-synthetic polymers such as cellulose, starch, alginates, polysaccharide derivatives, synthetic polymers such as vinyl polymers such as polyvinyl alcohol, polyvinylpyrrolidone, polyvinyl methyl ether, carboxyvinyl polymers, alkyl-modified carboxyvinyl polymers (acrylate-alkyl methacrylate copolymer, etc.) and sodium polyacrylate, and also polyethylene glycol and ethylene oxide-propylene oxide block copolymers.

SUMMARY OF THE INVENTION

The present invention provides an aqueous cosmetic or dermatological preparation which is suitable for application on wet or moist skin. The preparation comprises
(i) at least two (for example, at least three) different polyacrylic acid polymers,
(ii) at least two (for example, at least three) different $C_{14-22}$ fatty alcohols, and at least about 13% by weight of
(iii) microcrystalline wax, based on the total weight of the preparation.
Furthermore, the preparation is substantially emulsifier-free.

In one aspect, the polyacrylic acid polymers (i) may comprise (e.g., consist of) polymers selected from acrylates/C10-30 alkyl acrylate crosspolymers and carbomers. For example, the preparation may comprise two different acrylates/C10-30 alkyl acrylate crosspolymers (having different properties) and one carbomer. The weight ratio of the two different acrylates/C10-30 alkyl acrylate crosspolymers may, for example, be from about 3:1 to about 1:3, e.g., from about 2:1 to about 1:2, or about 1:1. The weight ratio of the two different acrylates/C10-30 alkyl acrylate crosspolymers (together) to the carbomer may, for example be from about 20:1 to about 5:1, e.g., from about 12:1 to about 8:1, or about 10:1.

In another aspect, the polyacrylic acid polymers of component (i) may comprise at least one polymer having emulsifying properties and/or at least one polymer which improves the sensory properties and/or increases the stability of the preparation, especially at elevated temperatures.

In another aspect of the preparation of the present invention, the preparation may comprise a total of from about 0.05% to about 2% by weight, e.g., a total of from about 0.2% to about 1% by weight, or a total of from about 0.2 to about 0.5% by weight of component (i), based on the total weight of the preparation.

In another aspect, the preparation may comprise a total of from about 3% to about 14% by weight, e.g., from about 4% to about 12% by weight, or a total of from about 7% to about 9% by weight of component (ii), based on the total weight of the preparation.

In another aspect, component (ii) may comprise at least one $C_{14}$ fatty alcohol (C14), at least one $C_{18}$ fatty alcohol (C18) and at least one $C_{16}/C_{18}$ fatty alcohol mixture (C16/C18). For example, in the weight ratio of the fatty alcohols C14, C18 and C16/18, a:b:c, a may range from about 0.5 to about 2, b may range from about 1 to about 3, and c may range from about 2 to about 6. For example, a may be 1, b may be about 2, and c may be about 5.

In another aspect of the preparation, component (ii) may comprise at least two (e.g., all) of myristyl alcohol, stearyl alcohol, and cetearyl alcohol.

In another aspect, the preparation may comprise from about 0.5% to about 2% by weight (e.g., from about 1% to about 2% by weight) of $C_{14}$ fatty alcohols, from about 1.5% to about 3.5% by weight (e.g., from about 2% to about 3% by weight) of $C_{18}$ fatty alcohols and from about 4% to about 6% by weight (e.g., from about 4.5% to about 5.5% by weight) of $C_{16}/C_{18}$ fatty alcohol mixture, based on the total weight of the preparation.

In yet another aspect, the preparation of the present invention may comprise at least about 15% by weight, e.g., at least about 16% by weight of component (iii).

In another aspect, the preparation may comprise not more than about 35% by weight, e.g., not more than about 30% by weight, or not more than about 25% by weight of component (iii).

In a still further aspect, the preparation of the present invention may further comprise, as component (iv), one or more hydrocarbon oils. For example, the preparation may comprise at least about 5% by weight, e.g., at least about 7% by weight of component (iv), based on the total weight of the preparation and/or the weight ratio component (iii):component (iv) may be from about 3:1 to about 1:1, e.g., about 2:1.

In another aspect, the preparation may comprise a total of component (iii) plus component (iv) of at least about 20% by weight, e.g., at least about 22% by weight, or at least 25% by weight and not more than about 60% by weight, e.g., not more than about 45% by weight, not more than about 40% by weight, or not more than about 35% by weight, based on the total weight of the preparation.

In another aspect of the preparation of the present invention, the preparation may further comprise at least about 45% by weight, e.g., at least about 50% by weight, or at least about 55% by weight, but usually not more than about 70% by weight, e.g., not more than about 65% by weight, or not more than about 60% by weight of water, based on the total weight of the preparation.

In another aspect of the preparation of the present invention, the preparation may further comprise at least one moisturizer. For example, the at least one moisturizer may comprise glycerol and the preparation may comprise, for example, at least about 4% by weight, e.g., at least about 5% by weight, at least about 10% by weight, or at least about 15% by weight of glycerol, based on the total weight of the preparation.

The present invention also provides an aqueous cosmetic or dermatological preparation which is suitable for application on wet or moist skin. The preparation comprises at least about 50% by weight of water, is substantially emulsifier-free and surfactant-free and comprises from about 0.2% to about 1% by weight of (i) at least three different polyacrylic acid polymers of which at least one has emulsifying properties and at least one improves the sensory properties (e.g., upon absorption of free water) and/or increases the stability of the preparation (particularly at elevated temperatures), from about 7% to about 9% by weight of (ii) at least three different $C_{14-22}$ fatty alcohols, from about 16% to about 30% by weight of (iii) microcrystalline wax, and at least about 6% by weight of (iv) one or more hydrocarbon oils, based on the total weight of the preparation. Furthermore, the weight ratio (iii):(iv) is from about 1.5:1 to about 2.5:1, e.g. about 2:1.

In one aspect, the preparation may further comprises at least about 5% by weight of glycerol, based on the total weight of the preparation.

The present invention also provides a method of caring for skin. The method comprises applying a preparation according to the present invention as set forth above (including the various aspects thereof) to (preferably wet or moist) skin. Preferably the method comprises using the preparation during showering or bathing and/or in combination with water having a temperature of at least about 30° C. and usually not higher than about 40° C. (e.g., not higher than about 35° C.) and/or subsequent to the cleansing of the skin or body.

The present invention also provides a method of wet shaving. The method comprises applying the preparation according to the present invention as set forth above (including the various aspects thereof) to (wet) skin prior to shaving by a wet shaving method.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

The preparation according to the present invention is substantially free of (conventional) emulsifiers. In this regard, it is pointed out that the term "emulsifier" as used herein and in the appended claims does not include polyacrylic acid polymers having emulsifying properties, which polymers may be comprised in component (i) of the preparation. On the contrary, a preparation according to the present invention preferably comprises at least one polyacrylic acid polymer that has emulsifying properties. Put another way, besides polyacrylic acid polymer(s), no further emulsifiers are present in the preparation according to the invention in any significant (emulsifying) concentration. It further is pointed out that the term "substantially" in connection with "emulsifier-free" is intended to indicate that the preparation does not contain any emulsifier or combination of emulsifiers in a concentration which would result in a noticeable emulsification. Accordingly, the concentration of emulsifier(s) in the instant preparation, if present at all, will usually be not higher than about 0.02%, e.g., not higher than 0.01% or not higher than 0.001% by weight, based on the total weight of the preparation (not including any polyacrylic acid polymer(s) which may be comprised in component (i)).

The preparation of the present invention comprises at least two (e.g., two, three, four or more, preferably at least three) different polyacrylic acid polymers, i.e., polyacrylic acid polymers which differ from each other with respect at least one of their properties.

The term "polyacrylic acid polymers" as used herein and in the appended claims denotes the polymers of acrylic acid and/or methacrylic acid as well as acrylate crosspolymers known in cosmetics. Preferably they include polymers (macromolecules) with a high molecular weight (>1 Mg/mol) which comprise a backbone of polyacrylic acid and small amounts of polyalkenyl ether crosslinkages. They are also referred to as carbomers. Carbomers are divided for example into types A, B and C. They differ, for example, in forming gels with different viscosities (United States Pharmacopoeia, USP). These water-soluble or dispersible polymers can bring about a significant viscosity increase in the liquid in which they are dissolved or dispersed. This is brought about by the formation of carbomer microgels in the water.

Other preferred polyacrylic acid polymers for use in the present invention include acrylate crosspolymers which exert a polymeric emulsifier effect. Polymeric emulsifiers are primarily polyacrylic acid polymers with a high molecular weight. These emulsifying polyacrylic acid polymers comprise a small lipophilic fraction in addition to the hydrophilic main part. Preferred within the context of the present invention are acrylate crosspolymers having the INCI name "Acrylates/C10-30 Alkyl Acrylate Crosspolymer". Representatives thereof are available, for example, under the trade names Pemulen® TR-1 and Pemulen® TR-2 and also Carbopol® 1342, Carbopol® 1382 and Carbopol® ETD 2020 from NOVEON. Preferred acrylates/C10-30 alkyl acrylate crosspolymers for use in the present invention include Pemulen® TR-1 and Carbopol® 3128 from Lubrizol.

A preferred combination of polyacrylic acid polymers for use in the present invention includes a polyacrylic acid polymer with emulsifying effect, such as Pemulen® TR-1 combined with other polyacrylic acid polymers, such as Carbopol® 3128, which improve the sensory properties and ensure the stability of the preparation (especially at elevated temperatures) and the combination with free water.

Particular preference is given to a combination of (at least) three polyacrylic acid polymers, i.e., (a) (at least) one polyacrylic acid polymer having an emulsifying effect, such as e.g. Pemulen® TR-1 or Pemulen® TR-2, combined with (b) (at least) one polyacrylic acid polymer which improves the sensory properties and ensures the stability of the preparation, especially at elevated temperatures (e.g. Carbopol® 3128) and (c) (at least) one polyacrylic acid polymer which improves the sensory properties upon absorbing free water (e.g. Carbopol® 981). Merely by way of example, component (i) of the preparation according to the present invention may comprise a total of from about 0.05% to 1% by weight, e.g., of from about 0.09% to about 0.25% by weight of (a) plus (b) (e.g., in a weight ratio of from about 2:1 to about 1:2 such as about 1:1) and from about 0.05% to about 1% by weight, e.g., from about 0.01% to about 0.03% by weight, of (c). For example, the preparation may comprise a combination of (1) from about 0.08% to about 0.15% by weight of Pemulen® TR-1 (and/or Pemulen® TR-2), (2) from about 0.08% to about 0.15% by weight of Carbopol® 3128, and (3) from about 0.01% to about 0.03% by weight of Carbopol® 981.

Component (i) will usually be present in the preparation of the present invention in a (total) concentration of at least about 0.05% by weight, e.g., at least about 0.1% by weight, at least about 0.15% by weight, or at least about 0.2% by weight, but usually not higher than about 1% by weight, e.g., not higher than about 0.5% by weight, not higher than about 0.3% by weight, or not higher than about 0.25% by weight.

The polyacrylic acid polymers which are comprised in the preparation of the present invention may also differ in the viscosities they provide. For example, when measured in a 0.2% by weight solution at 25° C. with a Brookfield RVT or RVF at 20 rpm with a spindle No. 5, Pemulen® TR-1 shows a minimum/maximum emulsion viscosity of 6,500/15,500 mPas, whereas the corresponding values for Carbopol® 1342 are 4,000/11,000 mPas.

Regarding component (ii) of the preparation of the present invention, $C_{14-22}$ fatty alcohols denote fatty alcohols having a carbon number from 14 to 22, e.g., 14, 16, 18, 20 or 22 carbon atoms. Preferably, the fatty alcohols are selected from linear (saturated) fatty alcohols and in particular, from one or more of myristyl alcohol ($C_{14}H_{30}O$), cetyl alcohol (or palmityl alcohol) ($C_{16}H_{34}O$), stearyl alcohol (or octadecyl alcohol) ($C_{18}H_{38}O$), and cetylstearyl alcohol (cetearyl alcohol), a mixture of predominantly cetyl alcohol (hexadecanol) and stearyl alcohol (octadecanol), (CAS No. 8005-44-5).

The preparation advantageously comprises at least three $C_{14\text{-}22}$ fatty alcohols and in particular, at least one $C_{14}$ fatty alcohol (C14), at least one $C_{18}$ fatty alcohol (C18) and at least one $C_{16}/C_{18}$ fatty alcohol mixture (C16/C18) is present, preferably in each case only one $C_{14}$ fatty alcohol, one $C_{18}$ fatty alcohol and one $C_{16}/C_{18}$ fatty alcohol mixture. If only two fatty alcohols are to be employed, the $C_{14}$ fatty alcohol is preferably absent.

Usually the $C_{14\text{-}22}$ fatty alcohols will be present in the preparation of the present invention in a total concentration of at least about 3% by weight, e.g., at least about 4% by weight, at least about 5% by weight, at least about 6% by weight, or at least about 7% by weight, but not higher than about 14% by weight, e.g., not higher than about 13% by weight, not higher than about 12% by weight, not higher than about 11% by weight, not higher than about 10% by weight, or not higher than about 9% by weight, based on the total weight of the preparation.

The weight percentages of the fatty alcohols will often be from about 0.5% to about 2.5% by weight for C14 fatty alcohol(s) (C14), from about 1.5% to about 4.0% by weight for C18 fatty alcohol(s) (C18) and from about 3.5% to about 6% by weight for C16/C18 fatty alcohols (C16/18), based on the total weight of the preparation. For example, the fatty alcohols contained in the preparation of the present invention may comprise or consist of (1) from about 0.5% to about 2.0% by weight of myristyl alcohol, (2) from about 1.5% to about 3.5% by weight of stearyl alcohol, and (3) from about 3.5% to about 6% by weight of cetearyl alcohol. Component (1) may optionally be absent.

The combination of at least two polyacrylic acid polymers and at least two $C_{14\text{-}22}$ fatty alcohols aids in the stabilization of the preparation of the present invention. If in each case only one representative of the polyacrylic acids and fatty alcohols is selected, the stability tends to be inadequate and in particular the skin feel upon application to moist/wet skin tends to be unpleasant, waxy, harsh, squeaky.

Regarding component (iii) of the preparation of the present invention, microcrystalline wax is a generic term and alternative names therefor include Cera Microcristallina [German: Mikrokristalline Wachse, French: Cire Minerale]. Microcrystalline wax (cera microcristallina) is a type of wax produced by de-oiling petrolatum, as part of the petroleum refining process. In contrast to the more familiar paraffin wax which contains mostly unbranched alkanes, microcrystalline wax contains a higher percentage of isoparaffinic (branched) hydrocarbons and naphthenic hydrocarbons. It exhibits finer crystals than paraffin wax. It predominantly consists of high molecular weight saturated aliphatic hydrocarbons having more than 35 carbon atoms in the molecule. It is generally darker, more viscous, denser, tackier and more elastic than paraffin wax, and has a higher molecular weight and melting point. The elastic and adhesive characteristics of microcrystalline wax are related to the non-straight chain components which it contains. Typical microcrystalline wax crystal structure is small and thin, making it more flexible than paraffin wax. A microcrystalline wax which is suitable for use in the present invention has the CAS No. 63231-60-7 (and or EINECS/EILINCS No. 264-038-1).

Microcrystalline wax when produced by wax refiners is typically produced to meet a number of ASTM specifications such as congeal point, needle penetration, color, and viscosity. Microcrystalline wax can generally be categorized into "laminating" grades and "hardening" grades. The laminating grades typically have a melting point of 140-175 F and a needle penetration of 25 or above. The melting point of hardening grades will usually range from about 175-200 F, and the needle penetration thereof will usually be 25 or below. Both grades are suitable for use in the present invention.

Microcrystalline wax is derived from the refining of the heavy distillates from lubricant oil production. This by-product then must be de-oiled at a wax refinery. Depending on the end use and desired specification, the product then may have its odor removed and color removed. This is usually done by means of a filtration method or by hydro-treating the wax material.

Microcrystalline wax for use in the instant invention will usually be subject to high quality standards. The microcrystalline wax for use in the instant invention usually will be substantially free from, for example, polycyclic aromatics, sulfur-containing compounds and other allergens such as, e.g., crop protection agents. Due to its chemical neutrality microcrystalline wax has no allergenic potential. Allergenic reactions triggered by microcrystalline wax are hitherto unknown. Compared to animal or plant oils, microcrystalline wax has a high oxidation stability, i.e., does not become rancid and requires no additional stabilizers. Microcrystalline wax and thus, also the preparations containing it therefore also require no or relatively small amounts of additional preservatives.

The skin care properties of microcrystalline wax are primarily in the area of skin moisturization. Microcrystalline wax forms a partially occlusive protective film on the skin which protects it against drying out. This is very important particularly in the case of dry skin or highly stressed skin with a damaged skin barrier. Partially occlusive care products position themselves in the upper horny layer and thereby reduce the transepidermal water loss. In combination with skin moisturizers (e.g., glycerol), they help to rapidly restore the equilibrium of the skin. It is noted that very similar substance mixtures, the so-called mineral waxes, are naturally present in relatively large amounts also in various plant waxes (e.g. candelilla wax) and insect waxes (e.g. beeswax).

Microcrystalline wax is present in the preparation of the present invention in a concentration of at least about 13% by weight, e.g., at least about 14% by weight, at least about 15% by weight, or at least about 16% by weight, and will usually be present in a concentration of not higher than about 40% by weight, e.g., not higher than about 35% by weight, not higher than about 30% by weight, or not higher than about 25% by weight.

In addition to components (i), (ii) and (iii), the preparation of the instant invention preferably also comprises component (iv), i.e., one or more hydrocarbon oils. A preferred hydrocarbon oil for use in the instant invention includes medical white oil, also called paraffinum liquidum. Medical white oils are substance mixtures which have a varying composition depending on origin. For example, products which have been obtained from geologically old Venezuelan petroleum are particularly rich in naphthenes (cycloalkanes). By contrast, the geologically young North Sea oil is low in naphthenes and comprises predominantly acyclic compounds.

Naphthene-rich mineral oils only occur in selected areas of the world (Venezuela, Saudi Arabia, Russia). They are difficult to obtain and accordingly expensive. Low-naphthene mineral oils are easier to obtain and are rather to be classed as good value. A disadvantage of the low-naphthene mineral oils is that these oils or mixtures with these oils with, inter alia, microcrystalline wax used in emulsions destabilize the emulsions, which results in a severe oil separation.

Naphthenes or alicyclic hydrocarbons are ring-shaped hydrocarbons. The naphthene content of crude oil is generally 5%, in the case of Russian oil it is often more than this, and in the case of American oil below this. Naphthenes have a higher bond tension than paraffins in the molecular structure and therefore have a higher heating value.

Cycloalkanes (cycloparaffins) are saturated ring-shaped hydrocarbons of the general formula $C_nH_{2n}$ (n=3, 4, 5 . . . ), the names of which are formed from that of the corresponding alkane and the prefix cyclo-. The cycloalkanes, inter alia, cyclopentane and cyclohexane, occurring in petroleum are also called naphthenes.

Preferably, naphthene-containing medical white oil is used in the preparation of the instant invention.

Component (iv) will usually be present in the preparation of the present invention in a concentration of at least about 5% by weight, e.g., at least about 6% by weight, at least about 7% by weight, or at least about 8% by weight. Further, the total concentration of components (iii) plus (iv) will often be at least about 20% by weight, e.g., at least about 22% by weight, or at least about 25% by weight, but will usually be not higher than about 60% by weight, e.g., not higher than about 50% by weight, not higher than about 40% by weight, or not higher than about 35% by weight, based on the total weight of the preparation. The weight ratio component (iii):component (iv) preferably is from about 3:1 to about 1:1, e.g., from about 1.5:1 to about 2.5:1.

In many cases a long-lasting and detectable, sensorily attractive film will be obtained on the skin only when the combined concentration of components (iii) plus (iv) is at least about 20% by weight. At total concentrations above about 60% by weight the preparation often can no longer be easily spread and becomes cream-like. The higher the total concentration of (iii) plus (iv), the higher the consistency and/or solidity as well, although this may be desired in specific preparations.

In this regard, it is noted that mixtures of components (iii) and (iv) are sometimes also referred to as "microcrystalline wax", "cera microcristallina" or "vaseline" (now a registered trade name of CheseBorough Ponds). However, as used herein and in the appended claims the term "microcrystalline wax" denotes exclusively component (iii), i.e., without component (iv).

Due to the relatively high concentration of microcrystalline wax, i.e., component (iii), in the preparation of the present invention only non-polar to medium-polar lipids (including, e.g., esters of glycerol and fatty acids) are advantageously present, if at all, in the preparation (in addition to component (iv)). Otherwise, the stability is more difficult to establish due to the substantial absence of (conventional) emulsifiers. At any rate, silicone oils are preferably not present in the preparation of the present invention. If they are present, their concentration will usually not be higher than about 1% by weight, e.g., not higher than about 0.5% by weight, or not higher than about 0.1% by weight.

Within the context of the present disclosure, the expression "lipids" is used as a generic term for fats, oils, waxes and the like, as is well known to the person skilled in the art. The terms "oil phase" and "lipid phase" are also used synonymously.

Oils and fats differ inter alia in their polarity. It is suggested to adopt the interfacial tension towards water as a measure of the polarity index of an oil or of an oil phase. In this case, the greater the polarity of the oil phase in question, the lower the interfacial tension between this oil phase and water. According to the invention, the interfacial tension is considered to be one possible measure of the polarity of a given oil component.

The interfacial tension is the force which acts on an imaginary line located at the interface between two phases and one meter in length. The physical unit for this interfacial tension is classically calculated according to the relationship force/length and is usually given in mN/m (millinewtons divided by meters). It has a positive sign if it strives to make the interface smaller. In the converse case, it has a negative sign.

The preparation according to the invention permits for the first time the application of care under the shower or in a bath tub, although the preparation can also be applied to advantage on skin that is not wet or moist.

The preparation according to the invention is advantageously formulated only with preservatives which have a solubility in water of more than 0.75% at 20° C. Due to the substantial absence of emulsifiers, the result may otherwise be destabilizations and crystallizing out. Preferably, the one or more preservatives include at least phenoxyethanol (solubility in water at 20° C. about 2.4% by weight); preferably, they will not include methylisothiazolinone and/or parabens such as methyl paraben.

The preparations according to the invention are advantageously prepared differently to customary polyacrylic acid-containing preparations. Current practice is to predisperse the "dusty" polyacrylic acids in a lipid and then to introduce them into the water phase. In the case of the preparations according to the invention, the polyacrylic acid polymers are dispersed in water because otherwise a barely perceptible residue is present and can be felt on the skin. As a result of this mode of preparation, the polyacrylic acid becomes more "activated" than if wetted with lipid.

Preparations according to the invention can, moreover, also be used as pre-shaving product in order to improve the shaving result. As a result of the long-lasting lipid/polymer film, the razor blade glides easily and can also grasp deeper hairs.

The preparation according to the present invention is preferably also substantially free of surfactants. In other words, one or more surfactants are preferably present, if at all, in a concentration which does not noticeably reduce the surface tension. Usually, total concentrations of surfactants, if present at all, in the preparation of the present invention are not higher than about 0.02%, e.g., not higher than 0.01%, or not higher than about 0.001% by weight, based on the total weight of the preparation.

Surfactants are substances which lower the surface tension of a liquid or the interfacial tension between two phases and permit or support the formation of dispersions. Surfactants enable two liquids that are actually not miscible with one another, such as, for example, oil and water, to be dispersed.

Furthermore, surfactants are described as amphiphilic substances which are able to dissolve organic, nonpolar substances in water. As a result of their specific molecular structure with at least one hydrophilic and one hydrophobic molecular moiety, they provide for a reduction in the surface tension of the water, the wetting of the skin, the facilitation of soil removal and dissolution, ease of rinsing off and—if desired—for foam regulation.

The hydrophilic moieties of a surfactant molecule are mostly polar functional groups, for example —COO$^-$, —OSO$_3^{2-}$, —SO$_3^-$, whereas the hydrophobic moieties are generally nonpolar hydrocarbon radicals. Surfactants are generally classified according to type and charge of the hydrophilic molecular moiety. In this connection, four groups can be differentiated:

anionic surfactants, cationic surfactants, amphoteric surfactants and nonionic surfactants.

Anionic surfactants generally have carboxylate, sulfate or sulfonate groups as functional groups. In an aqueous solution, they form negatively charged organic ions in an acidic or neutral medium. Cationic surfactants are almost exclusively characterized by the presence of a quaternary ammonium group. In an aqueous solution, they form positively charged organic ions in an acidic or neutral medium. Amphoteric surfactants contain both anionic and cationic groups and accordingly behave like anionic or cationic surfactants in aqueous solution depending on the pH. In a strongly acidic medium, they have a positive charge, and in an alkaline medium they have a negative charge.

Furthermore, detergent substances are known, such as, for example, cationic surfactants, in particular quaternary ammonium compounds. A detergent substance is used in laundry detergents, dishwashing detergents, shampoos, shower gels and refers to the fraction of the formulation which influences the washing or cleaning performance. Detergent substances increase the "solubility" of fat and dirt particles in water which adhere in the laundry or on the body. They can be of natural or synthetic origin. They are differentiated into anionic, cationic, ampholytic or nonionic depending on the nature of their charge.

Emulsifiers enable two immiscible liquids (for example oil in water) to be combined to give an emulsion. Due to their amphiphilic character, they penetrate into the oil with their fat-soluble moiety. As a result of the hydrophilic moiety, the oil droplet that is now formed by stifling can be dispersed in the aqueous environment. Emulsifiers have primarily no detergent, surface tension lowering character.

Preferred preparations according to the present invention include a preparation which comprises, based on the total weight of the preparation:

from about 14% to about 18% by weight of microcrystalline wax;

from about 6% to about 10% by weight of medical white oil (paraffinum liquidum);

from about 0.01% to about 0.03% by weight of (at least) one polyacrylic acid polymer A which improves the sensory properties upon absorbing free water (e.g. Carbopol® 981);

from about 0.07% to about 0.12% by weight of (at least) one polyacrylic acid polymer B having an emulsifying effect, (e.g. Pemulen® TR-1 and/or Pemulen® TR-2);

from about 0.07% to about 0.12% by weight of (at least) one polyacrylic acid polymer C which improves the sensory properties and ensures the stability of the preparation, especially at elevated temperatures (e.g. Carbopol® 3128);

from about 0.7% to about 1.2% by weight of myristyl alcohol;

from about 1.5% to about 2.5% by weight of stearyl alcohol; and from about 4.5% to about 5.5% by weight of cetearyl alcohol.

Polyacrylic acid polymer C and/or myristyl alcohol may optionally be absent from the above preparation. In this case the concentration of polyacrylic acid polymer B may be up to about 0.15% by weight and/or the concentration of stearyl alcohol may be up to about 3.5% by weight.

The preparation according to the present invention may also comprise cosmetic auxiliaries and further active ingredients as are customarily used in cosmetic preparations such as, e.g., dyes and coloring pigments, moisturizing and/or humectant substances (such as, e.g., glycerol, urea, and certain amino acids), fillers (such as, e.g., aluminum starch octenylsuccinate), foam stabilizers, UV filter substances, electrolytes (e.g., sea salt), fragrance and organic solvents, provided they do not adversely affect the desired properties of the preparation.

The preparation of the present invention may moreover comprise one or more active ingredients which have a positive influence on skin. Active ingredients for use in the present invention preferably exhibit a skin moisturizing effect and/or strengthen the barrier function of skin and/or promote the restructuring of the connective tissue and/or support the function of dry skin and/or positively influence irritated skin (both sensitive skin in general and skin irritated by noxae such as UV light or chemicals) and/or reduce wrinkles and/or protect esthetically unattractive skin such as aged skin and/or improve the appearance of dry or rough skin and/or reduce hyperpigmentation, hypopigmentation, defective pigmentation and/or age spots and/or reduce itching and/or visible blood vessel dilation such as teleangiektasis or cuperosis.

Non-limiting specific examples of active ingredients which may be comprised in the preparation of the present invention include bioquinones such as, e.g., ubiquinone Q10, isoflavone and isoflavonoids as well as isoflavonoid containing plant extracts such as soy and clover extracts, flavonoids, genistein, arctiin, cardiolipin, anti-freezing proteins, hop extracts, hop-malt extracts, ascorbic acid and derivatives thereof, tocopherol and esters thereof, biotin, creatine, creatinine, propionic acid, green tea extracts and solutions, white tea extracts or solutions, sericosides, various extracts of licorice root, licochalcone A, silymarin, silyphos, dexpanthenol, ethanol, inhibitors of the prostaglandin metabolism and in particular, cyclooxygenase inhibitors, inhibitors of the leucotriene metabolism and in particular, 5-lipoxygenase inhibitors, inhibitors of the 5-lipoxygenase inhibitor protein, FLAP, folic acid, phytoene, flavone glycosides such as, e.g., α-glucosylrutin, carnitine, polydocanol, carotenoids, taurine, dihydroxyacetone, 8-hexadecene-1,16 dicarboxylic acid, retinol and esters thereof, vitamin E and derivatives thereof, long chain hyaluronic acids (e.g., those having an average molecular weight of from 1 to 3 million Dalton), and short chain hyaluronic acids (e.g., those having an average molecular weight of from 5,000 to 1 million Dalton).

The one or more active ingredients, if present, will usually be present in a total concentration of from about 0.1% to about 30% by weight, based on the total weight of the preparation.

It has surprisingly been found that the preparation of the present invention can increase the availability of certain active ingredients and other optional components contained therein. In other words, the same effect is achieved with a lower amount of component. This is a significant advantage for the consumer because many optional components such as, e.g., perfume oils contain constituents which can trigger allergic reactions and the like. Thus, reducing the concentration of these components without reducing their effect is also an advantage with respect to mildness and tolerability of the preparation.

The viscosity of a preparation of the present invention will usually be not lower than about 1,000 mPas, e.g., not lower than about 2,000 mPas, not lower than about 3,000 mPas, or not lower than about 3,500 mPas, but usually not higher than about 10,000 mPas, e.g., not higher than about 8,000 mPas, not higher than about 7,000 mPas, not higher than about 6,000 mPas, or not higher than about 5,500 mPas, as measured at 25° C. 24 hours after preparing the preparation by means of a rotational rheometer such as, e.g., the apparatus Rheomat R 123 of proRheo GmbH, Germany (spindle No. 1).

The preparation of the present invention may particularly advantageously be used on wet or moist skin (and also for (wet) shaving). In particular, the preparation may be used while showering or bathing and following the cleansing of the skin/body. Following the application of the preparation rinsing with water and drying the skin with, e.g., a towel are all that is needed for obtaining the skin care effect of the preparation. Parts of the preparation are left behind on the skin in a manner similar to applying a cream onto the skin. In other words, the preparation may be used as a balm similar to the use of a hair conditioner after cleansing the hair.

The preparation of the present invention may be provided in any container which is suitable for cosmetic or dermatological compositions. For example, it may be placed in a (plastic) bottle, e.g., a bottle that is to be stored upside down.

The examples below illustrate the preparation according to the invention. The numerical values represent percent by weight, based on the total weight of the preparation.

Comparative Testing

Preparation A according to the invention set forth in the table below was compared sensorily by trained test subjects (60) with a preparation B comprising emulsifiers, and a preparation C comprising only one fatty alcohol and only one polyacrylic acid polymer.

| Preparation | A | B | C |
|---|---|---|---|
| Mixture of microcrystalline wax (66) and medical white oil (34) (concentration of microcrystalline wax) | 25.0000 (16.5) | 25.0000 (16.5) | 25.0000 (16.5) |
| Myristyl alcohol | 1.0000 | 1.0000 | 1.0000 |
| Cetearyl alcohol | 5.0000 | 5.0000 | |
| Stearyl alcohol | 2.0000 | 2.0000 | |
| Hydrogenated coco-glycerides | 3.0000 | 3.0000 | 3.0000 |
| Glyceryl stearate SE | | 1.0000 | |
| Glyceryl stearate citrate | | 1.0000 | |
| Aluminum starch octenylsuccinate + water | 1.0000 | 1.0000 | 1.0000 |
| Perfume | 1.0000 | 1.0000 | 1.0000 |
| Glycerol | 5.1000 | 5.1000 | 5.1000 |
| Water + sodium hydroxide | 0.1600 | 0.1600 | 0.1050 |
| Phenoxyethanol | 0.5000 | 0.5000 | 0.5000 |
| Methylisothiazolinone | 0.0900 | 0.0900 | 0.0900 |
| Acrylates/C10-30 alkyl acrylate crosspolymer (Carbopol ® 3128) | 0.1000 | 0.1000 | |
| Carbomer (Carbopol ® 981) | 0.0200 | 0.0200 | |
| Acrylates/C10-30 alkyl acrylate crosspolymer (Pemulen ® TR-1) | 0.1000 | 0.1000 | 0.1500 |
| Water | ad 100 | ad 100 | ad 100 |

EXAMPLES

| Example No. | 1 | 2 | 3 | 4 | 5 | 6 |
|---|---|---|---|---|---|---|
| (1) Microcrystalline Wax | 16.500 | 16.500 | 16.500 | 23.100 | 29.700 | 29.700 |
| (2) Medical white oil | 8.500 | 8.500 | 8.500 | 11.900 | 15.300 | 15.300 |
| (1) + (2) | 25.000 | 25.000 | 25.000 | 35.000 | 45.000 | 45.000 |
| Myristyl alcohol | 1.0000 | 1.0000 | 1.0000 | 2.0000 | — | — |
| Cetearyl alcohol | 5.0000 | 5.0000 | 5.0000 | 4.0000 | 4.0000 | 4.0000 |
| Stearyl alcohol | 2.0000 | 2.0000 | 2.0000 | 3.0000 | 3.0000 | 3.0000 |
| Hydrogenated cocoglycerides | 3.0000 | 3.0000 | 3.0000 | 2.0000 | 2.0000 | 2.0000 |
| Almond oil | | | 0.3500 | | 0.7000 | 0.7000 |
| Aluminum starch octenylsuccinate | 1.0000 | 1.0000 | 1.0000 | 1.0000 | 1.0000 | 1.0000 |
| Perfume | 0.8000 | 0.7000 | 1.0000 | 0.7000 | 0.7000 | — |
| Glycerol | 5.1000 | 5.1000 | 5.1000 | 15.100 | 10.100 | 10.100 |
| Sodium hydroxide solution 45% strength | 0.1600 | 0.1600 | 0.1600 | 0.1600 | 0.1600 | 0.1600 |
| Phenoxyethanol | 0.5000 | 0.5000 | 0.5000 | 0.4000 | 0.4000 | 0.4000 |
| Methylisothiazolinone | 0.0900 | 0.0900 | 0.0900 | 0.0800 | 0.0800 | 0.0800 |
| Acrylates/C10-30 alkyl acrylate crosspolymer (Carbopol ® 3128) | 0.1000 | 0.1000 | 0.1000 | 0.1200 | — | — |
| Carbomer (Carbopol ® 981) | 0.0200 | 0.0200 | 0.0200 | 0.0200 | 0.0200 | 0.0200 |
| Acrylates/C10-30 alkyl acrylate crosspolymer (Pemulen ® TR-1) | 0.1000 | 0.1000 | 0.1000 | 0.1200 | 0.1400 | 0.1400 |
| Sea salt | 0.0100 | 0.0100 | | 0.0100 | 0.0500 | 0.0500 |
| Water | ad 100 | ad 100 | ad 100 | ad 100 | ad 100 | ad 100 |

Results

| Preparation | A | C |
| --- | --- | --- |
| The product can be easily spread | 6.1 | 5.1 |
| The product feels pleasant after showering off | 5.9 | 5.1 |
| The skin does not tighten | 6.3 | 5.8 |

| Preparation | A | B |
| --- | --- | --- |
| The product can be washed off easily | 6 | 5.5 |
| The product feels pleasant after showering off | 5.9 | 5.2 |
| The skin does not tighten | 6.3 | 5.8 |
| The skin feels cared for | 5.7 | 4.9 |

The higher the value, the better (scale from 0-7).

The results surprisingly show that preparations with only one fatty alcohol can be spread less easily; further, preparation (C) feels unpleasant after showering off and a feeling of tightness remains on the dry skin (comparison preparation A versus C).

It is likewise found that the preparation with emulsifiers can be washed off less readily, the skin feel after showering off is more unpleasant and the skin exhibits a feeling of tightness (comparison preparation A versus B).

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The entire disclosure of copending application entitled "FIXING OF PERFUME ON WET SKIN", filed concurrently herewith Ser. No 13/606,570, is expressly incorporated by reference herein.

What is claimed is:

1. An aqueous cosmetic or dermatological preparation for application on wet or moist skin, wherein the preparation is substantially emulsifier-free and comprises (i) at least two different polyacrylic acid polymers, (ii) at least two different $C_{14-22}$ fatty alcohols, and at least about 13% by weight of (iii) microcrystalline wax, based on a total weight of the preparation.

2. The preparation of claim 1, wherein the preparation comprises at least three different polyacrylic acid polymers.

3. The preparation of claim 1, wherein the polyacrylic acid polymers (i) are selected from acrylates/C10-30 alkyl acrylate crosspolymers and carbomers.

4. The preparation of claim 1, wherein the polyacrylic acid polymers (i) comprise at least one polymer having emulsifying properties.

5. The preparation of claim 1, wherein the polyacrylic acid polymers (i) comprise at least one polymer which at least one of improves sensory properties of the preparation and increases a stability of the preparation.

6. The preparation of claim 1, wherein the preparation comprises a total of from about 0.05% to about 2% by weight of (i), based on the total weight of the preparation.

7. The preparation of claim 6, wherein the preparation comprises a total of from about 0.2% to about 1% by weight of (i).

8. The preparation of claim 1, wherein the preparation comprises at least three $C_{14-22}$ fatty alcohols.

9. The preparation of claim 1, wherein the preparation comprises a total of from about 3% to about 14% by weight of (ii), based on the total weight of the preparation.

10. The preparation of claim 9, wherein the preparation comprises a total of from about 7% to about 9% by weight of (ii).

11. The preparation of claim 1, wherein (ii) comprises at least one $C_{14}$ fatty alcohol (C14), at least one $C_{18}$ fatty alcohol (C18) and at least one $C_{16}/C_{18}$ fatty alcohol mixture (C16/C18).

12. The preparation of claim 11, wherein a weight ratio of the fatty alcohols C14, C18 and C16/18 is a:b:c, with a ranging from about 0.5 to about 2, b ranging from about 1 to about 3, and c ranging from about 2 to about 6.

13. The preparation of claim 12, wherein a is 1, b is about 2, and c is about 5.

14. The preparation of claim 1, wherein (ii) comprises at least two of myristyl alcohol, stearyl alcohol, and cetearyl alcohol.

15. The preparation of claim 1, wherein the preparation comprises from about 0.5% to about 2% by weight of $C_{14}$ fatty alcohols, from about 1.5% to about 3% by weight of $C_{18}$ fatty alcohols and from about 4% to about 6% by weight of $C_{16}/C_{18}$ fatty alcohol mixture, based on the total weight of the preparation.

16. The preparation of claim 1, wherein the preparation comprises at least about 15% by weight of (iii).

17. The preparation of claim 1, wherein the preparation comprises not more than about 35% by weight of (iii).

18. The preparation of claim 1, wherein the preparation further comprises (iv) one or more hydrocarbon oils.

19. The preparation of claim 18, wherein the preparation comprises at least about 5% by weight of (iv), based on the total weight of the preparation.

20. The preparation of claim 18, wherein a weight ratio (iii):(iv) is from about 3:1 to about 1:1.

21. The preparation of claim 18, wherein the preparation comprises a total of (iii) plus (iv) of from about 20% to about 60% by weight, based on the total weight of the preparation.

22. The preparation of claim 1, wherein the preparation comprises at least about 45% by weight of water, based on the total weight of the preparation.

23. The preparation of claim 1, wherein the preparation further comprises at least one moisturizer.

24. The preparation of claim 23, wherein the at least one moisturizer comprises glycerol.

25. The preparation of claim 24, wherein the preparation comprises at least about 4% by weight of glycerol, based on the total weight of the preparation.

26. An aqueous cosmetic or dermatological preparation for application on wet or moist skin, wherein the preparation comprises at least about 50% by weight of water, is substantially emulsifier-free and surfactant-free and comprises from about 0.2% to about 1% by weight of (i) at least three different polyacrylic acid polymers of which at least one has emulsifying properties and at least one at least one of improves sensory properties of the preparation and increases a stability of the preparation, from about 7% to about 9% by weight of (ii) at least three different $C_{14-22}$ fatty alcohols, from about 16% to about 30% by weight of (iii) microcrystalline wax, and at least about 6% by weight of (iv) one or more hydrocarbon oils, based on a total weight of the preparation, a weight ratio (iii):(iv) being from about 1.5:1 to about 2.5:1.

27. The preparation of claim 26, wherein the preparation further comprises at least about 5% by weight of glycerol, based on the total weight of the preparation.

28. A method of caring for skin, wherein the method comprises applying the preparation of claim 1 to skin.

29. The method of claim 28, wherein the skin is wet or moist.

30. The method of claim 28, wherein the preparation is applied during bathing or under the shower.

31. The method of claim 28, wherein the preparation is applied subsequent to a cleansing of the skin.

32. A method of wet shaving, wherein the preparation comprises applying the preparation of claim 1 to skin prior to shaving by a wet shaving method.

\* \* \* \* \*